United States Patent [19]
D'Angelo et al.

[11] 3,952,041
[45] Apr. 20, 1976

[54] PEROXY COMPOUNDS CONTAINING AN ACID HALIDE GROUP

[75] Inventors: Antonio Joseph D'Angelo, Englishtown, N.J.; Orville Leonard Mageli, Kenmore, N.Y.

[73] Assignee: Pennwalt Corporation, Philadelphia, Pa.

[22] Filed: July 31, 1974

[21] Appl. No.: 493,369

Related U.S. Application Data

[60] Continuation of Ser. No. 211,092, Dec. 22, 1971, abandoned, which is a division of Ser. No. 727,323, May 7, 1968, Pat. No. 3,671,651.

[52] U.S. Cl. ............................................. 260/453 R
[51] Int. Cl.² ...................................... C07C 179/18
[58] Field of Search .............................. 260/453 R

[56] References Cited
UNITED STATES PATENTS 3,671,651   6/1972   D'Angelo .................... 260/453 R

OTHER PUBLICATIONS

D'Angelo et al., "Peroxide cmpds. and their use, etc."; (1970) CA 73 No. 36125r, (1970).

*Primary Examiner*—Glennon H. Hollrah
*Attorney, Agent, or Firm*—David Edwards

[57]   ABSTRACT

A novel class of compounds $X_n$—$R_p$—$Y_m$ where R is a 2–4 valent aliphatic, cycloaliphatic or aromatic radical; X is an acylating function; Y is a peroxy containing group and $n$ and $m$ are each equal to 1–2 and $p$ is at least 1.

7 Claims, No Drawings

PEROXY COMPOUNDS CONTAINING AN ACID HALIDE GROUP

CROSS-REFERENCE TO RELATED APPLICATIONS

This is a continuation of application Ser. No. 211,092 filed Dec. 22, 1971, now abandoned, which in turn is a division of application Ser. No. 727,323 filed May 7, 1968, now U.S. Pat. No. 3,671,651.

BACKGROUND OF THE INVENTION

This invention relates to novel compounds having both a peroxy group and an acylating function and to polymers having at least one peroxy group. Also the invention relates to methods for preparing compounds having both a peroxy group and an acylating function. Also the invention relates to a method of making block and graft polymers from vinyl-type monomers.

The Prior Art

Aliphatic t-alkyl peroxy chloroformate and di-t-alkyl and aralkyl peroxides containing acylating groups are known. A. G. Davies et al., J. Chem. Soc. (1953) p 1808 et seq. prepared aliphatic t-alkyl peroxy chloroformates, such as,

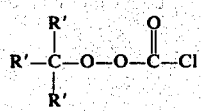

t-alkyl peroxy chloroformate by reacting t-alkyl hydroperoxide with phosgene. The following derivatives were also prepared by reaction of the

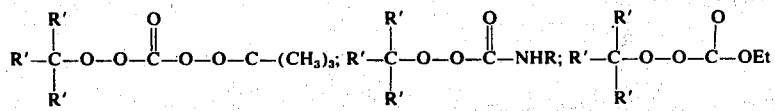

chloroformate with t-butyl hydroperoxide, amines and alcohols. (This type of peroxy compounds containing acylating groups do not fall within the scope of our invention because the peroxy group is not separated from the chloroformyl group and actually is a part of it.)

The di-t-alkyl peroxides containing acylating groups represented by the following structures

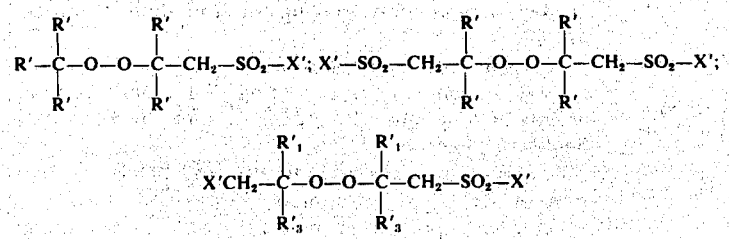

where $R'_1$ and $R'$ are lower alkyl radicals, $R'_3$ is lower alkyl or aromatic radical, $X'$ is either Cl or Br were prepared in U.S. Pat. No. 2,519,403. Derivatives prepared from the above structures were obtained by replacement of the halogen in $-SO_2-X'$ group with hydroperoxides, alcohols, ammonia, primary and secondary amines in U.S. Pat. No. 2,542,578. (These compounds do not fall within the scope of this invention because the connecting link is $-SO_2-$ rather than

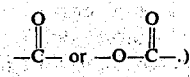

Di-t-aralkyl peroxides containing as acylating groups

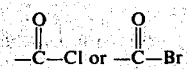

represented by the following structure:

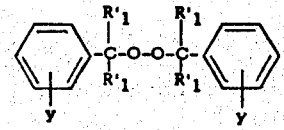

where $R'_1$ is the same or different alkyl radical and y is

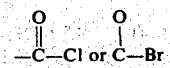

group were prepared in U.S. Pat. No. 3,165,546.

The above peroxy compounds do not come within this invention. They have many disadvantages:

1. They are too thermally stable to be useful for vinyl polymerization.
2. When reacted with polymers containing more than two functional groups, the polymer obtained is a crosslinked one which is not useful for block and graft work due to the inherent insolubility of crosslinked polymer in most organic solvents.
3. They can only be used in condensation reaction to prepare polyesters, polyamides, etc. and even in applications such as these, the resultant polymer, in order to be useful for block and graft work, an ouutside source of radiation has to be used in order to decompose the peroxide.
4. They do not offer a wide range of operating temperature which is so important when working with the preparation of graft and block copolymers from different vinyl monomers.

With peroxidic materials one of ordinary skill in the art would not use the reaction conditions necessary to convert any peroxy compound containing carboxylic or alcohol groups to the desired corresponding acid halide, anhydride and chloroformate. He would expect decomposition of the peroxide to take place especially with peroxides of the diperketals, perester, and diacyl type.

SUMMARY OF THE INVENTION

I. A class of compounds having at least one peroxy group and at least one acylating function defined by the following general formula:

$$X_n\text{-}R_p\text{-}Y_m \quad \text{I.}$$

where:
1. R is an aliphatic, cycloaliphatic or aromatic radical having 2–4 valences available for X and Y;
2. $p$ is an integer equal to at least 1;
3. X is $$-\overset{O}{\underset{\|}{C}}-B;$$

4. B is Cl— or Br—;
5. Y is selected from the class consisting of $$-\overset{O}{\underset{\|}{C}}-OO-R_1, \quad -\overset{O}{\underset{\|}{C}}-OO-\overset{O}{\underset{\|}{C}}-RX_n, \quad -\overset{O}{\underset{\|}{C}}-OO-\overset{(R_2)_2}{\underset{|}{C}}-C \quad \overset{(R_2)_2}{\underset{|}{C}}-\overset{(R_2)_2}{\underset{|}{C}}-OO-\overset{O}{\underset{\|}{C}}-RX_n,$$

$$-\overset{O}{\underset{\|}{C}}-OO-\overset{(R_2)_2}{\underset{|}{C}}-(CH_2)_q-\overset{(R_2)_2}{\underset{|}{C}}-OO-\overset{O}{\underset{\|}{C}}-RX_n, \quad -\overset{O}{\underset{\|}{C}}-OO-R_3, \quad (R_1-OO)_2-\overset{R_2}{\underset{|}{C}}-,$$

$$R_4-O-\overset{O}{\underset{\|}{C}}-OO-\overset{R_2}{\underset{|}{C}}, \quad R_1-OO-\overset{O}{\underset{\|}{C}}-O-, \quad R_1-OO-\overset{R_2}{\underset{|}{C}}-OO-\overset{R_2}{\underset{|}{C}}-,$$

$$R_4-O-\overset{O}{\underset{\|}{C}}-OO-\overset{O}{\underset{\|}{C}}-, \quad R_4-\overset{O}{\underset{\|}{C}}-OO-\overset{O}{\underset{\|}{C}}-O-, \quad (R_4O)_2\overset{O}{\underset{\uparrow}{P}}-OO-\overset{R_2}{\underset{|}{C}}-, \text{ and}$$

$$R_4-\overset{O}{\underset{\|}{C}}-OO-\overset{O\uparrow}{\underset{\downarrow}{S}}\\\underset{O}{}$$

6. $R_1$ is a tertiary alkyl group having 4–8 carbon atoms;
7. $R_2$ is aliphatic radical of 1 to 12 carbons or cycloaliphatic of 3 to 12 carbons.
8. $R_3$ is t-alkyl or aralkyl each having not more than 10 carbon atoms;
9. $R_4$ is aliphatic radical of 1 to 12 carbons; cycloaliphatic radical of 3 to 12 carbons; or aromatic radical of 6 to 12 carbons;
10. $n$ is an integer equal to 1–2;
11. $m$ is an integer equal to 1–2; and
12. $q$ is an integer equal to 2–4.

DESCRIPTION OF THE INVENTION

Compounds I

In the compound $X_n-R_p-Y_m$, R is aliphatic, cycloaliphatic or aromatic having 2–4 valences available for X and Y. More commonly these are hydrocarbon radicals of these types. Desirably the aliphatic hydrocarbon radical has 1–20 carbon atoms —preferably this is an alkyl radical. Desirably the cycloaliphatic hydrocarbon radical having 4–10 ring carbon atoms —preferably this is a cycloalkyl radical. Desirably the aromatic hydrocarbon radical has one or two benzene rings, which can be condensed as in naphthenylene or joined as in biphenylene.

X is an acylating function which may be an acid chloride or bromide.

Y is a peroxy containing group, as defined in the summary herein. Some of the defined groups also include an acylating function X, affording a compound having a multiplicity of acylating functions.

"$n$ and $m$" are integers each equal to 1–2; $n$ and $m$ need not be equal to each other.

$R_1$ is a tertiary alkyl group having 4–8 carbon atoms. This is to be understood as $$R''-\underset{\underset{R''}{|}}{\overset{|}{C}}-R''$$

where $R''$ is alkyl.

$R_2$ is an aliphatic group having 1–12 carbon atoms or cycloaliphatic group having 3–12 carbon atoms.

$R_4$ is an aliphatic radical of 1 to 12 carbons, cycloaliphatic radical of 3 to 12 carbons or an aromatic radical of 6 to 12 carbons.

$R_3$ is t-alkyl having not more than 10 carbon atoms or aralkyl, such as cumyl, having not more than 10 carbon atoms.

"$q$" is an integer equal to 2–4.

Two procedures for preparing compounds coming within "Compounds I" are set out in the Examples Section herein.

Compounds I are useful initiators for the polymerization of vinyl-type monomers. Compounds I can be reacted with polymeric materials containing terminal or pendant hydroxyl, amino, and mercapto groups or any other functionality that can be acylated. (Examples I, II). Compounds containing two acylating groups can be reacted with difunctional monomers to obtain condensation polymers like: polyesters, polyamides, etc. (Example IV) containing intermittant peroxy groups along the polymer backbone. These peroxy compounds containing acylating groups are useful as intermediate for the preparation of other derivatives and they will undergo any reaction where acid halides are normally used.

The peroxy containing polymers so prepared can in turn be used to make block and graft copolymers by treating them with polymerizable vinyl-type monomers under conditions where the peroxycarbon linkage is decomposed (ruptured) into free radicals at a rate and temperature suitable for polymerizing the vinyl monomer itself. Suitable vinyl-type monomers include: styrene, butadiene, isoprene, acrylonitrile, vinyl chloride, ethyl acrylate, methyl methacrylate, vinyl acetate, acrylic acid, vinyl stearate, vinylidene chloride, and the like.

Any of the conventional procedures for decomposing the peroxide, such as heating to the proper temperature, activation with amines or transition metal salts, and ultra violet irradiation can be used.

Illustrative block and graft polymers are prepared in Examples V, VI and VIII.

Method of Preparing Compound I

It has been discovered that compounds having both at least one peroxy group and at least one acylating function are produced by the acylation of a peroxide having a carboxyl group. No other group capable of reacting with the acylating agent is present in the peroxide reactant.

The acyl function forming reagent is phosphorus trichloride, phosphorus tribromide, phosphorus pentachloride, phosphorus pentabromide, sulfuryl chloride, sulfuryl bromide, thionyl chloride, or thionyl bromide.

The acylating reaction is carried out at a temperature suitable for the reaction but controlled to avoid substantial decomposition of the peroxy groups present in the reaction zone. The temperature will vary for particular reactant systems but, in general, falls in the range of about 0° to 80°C.

The method is illustrated by Procedures I and II in the Examples herein.

It has also been discovered that compounds having both, at least one peroxy group and at least one acylating function are prepared by peroxidizing a compound having at least two acylating functions, as the only peroxidizable substituents using the agent in an amount such that at least one acylatiing function is not peroxidized. The class of compounds possible by this method have the general formula $X_n$-$R_p$-$Y'_m$ where X, R, n, m and p have the definitions set out in respect to Compound I. Y' includes all the members set out in the definition of Y except for

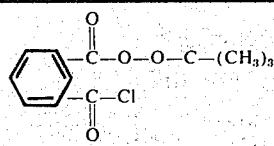

The peroxidizing agent may be a suitable organic hydroperoxide or in some instance an alkali metal peroxide.

EXAMPLES

Compounds of the invention containing an acylating group and a peroxy group were prepared by one of the following procedures:

Example of Procedure I

Preparation of t-butyl o-(chloroformyl) peroxybenzoate

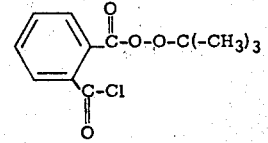

To a suspension of t-butyl o-(carboxy)peroxy-benzoate (16.2g. 0.06 moles) in 100 ml. of benzene at +6°C to +24°C but preferably at +6°C to +10°C was added in a single portion phosphorous pentachloride (12.6g. 0.06 moles).

The mixture was stirred for two hours or longer at +24°C to +80°C but preferably at +24°C to +40°C.

At the end of the reaction period the mixture was diluted with ice-water and the organic phase separated, washed to neutrality, dried over anhydrous magnesium sulfate, filtered and the solvent evaporated under reduced pressure.

A viscous liquid was obtained (14g).

Calculated yield for $C_{12}H_{13}Cl\ O_4$ 15.1g. or 92.7% of the theory. S.P.I, at 115°C gave: Gel Time 6.3 min.; Cure Time 7.9; Peak °F 443 Calculated A(O) 6.24%. Found 5.95% or 95.5% pure.

Example of Procedure II

Preparation of bis(4chloroformylbutyryl) peroxide

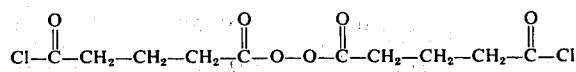

A mixture of glutaric acid peroxide (10.5g. 0.04 moles) and thionyl chloride (30 ml.) at 0° to +30°C preferably at +10°C to +24°C was treated with one drop or more of pyridine. The mixture was allowed to react for 24 hours or longer at +30° to +80°C but preferably at +30°C to +40°C. After this time the mixture was evaporated under reduced pressure.

A viscous liquid was obtained, (9g).

Calculated yield for $C_{10}H_{12}Cl_2O_6$ 11.9g. or 75.6% of the theory.

Calculated A(O) 6.35%, found A(O) 5.11%. Calculated %Cl 23.9 found Cl 25.2%.

Compounds prepared by one of these procedures are tabulated in Table I.

TABLE I

| Names & Structure | Chlorinating agent | % Yield uncorr. | Purity | Theor. (O) | Found (O) | Theor. Cl% | Found Cl% |
|---|---|---|---|---|---|---|---|
| 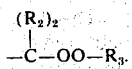 t-butyl o-(chloroformyl) peroxybenzoate | PCl$_5$ | 92.7 | 95.5 | 6.24 | 5.95 | — | — |

TABLE I-continued

| Names & Structure | Chlorinating agent | % Yield uncorr. | Purity | Theor. (O) | Found (O) | Theor. Cl% | Found Cl% |
|---|---|---|---|---|---|---|---|
| Cl—C(=O)—C₆H₄—C(=O)—OOC—(CH₃)₃ ; (CH₃)₃CO—O—C(=O)—C₆H₄—C(=O)—Cl<br>di-t-butyl 2,5-di(chloroformyl) di-peroxy-terphthalate | PCl₅ | — | 62 | 7.35 | 4.5 | 16.3 | 10.1 |
| (cyclohexyl-S)—C(=O)—OOC—(CH₃)₃ ; —C(=O)—Cl<br>t-butyl 2-(chloroformyl)-hexahydroperoxybenzoate | SOCl₂ | 99.8 | 100 | 6.2 | 6.2 | — | — |
| (CH₃)₃—C—OOC(=O)—CH=CH—C(=O)—Cl<br>3-(t-butylperoxycarbonyl)-acryloyl chloride | PCl₅ | 50 | 54.8 | 7.75 | 4.23 | — | — |
| (CH₃)₃C—OOC(=O)—CH₂—CH₂—C(=O)—Cl<br>3-(t-butylperoxycarbonyl)-propionyl chloride | PCl₅ | — | 98.5 | 7.7 | 7.59 | — | — |
| (Cl—C(=O)—CH₂—CH₂—CH₂—C(=O)—O)₂<br>bis(4-chloroformylbutyryl) peroxide | SOCl₂ | — | 95.5 | 5.35 | 5.11 | 23.9 | 25.2 |

Other compounds that can be prepared by conventional methods are:

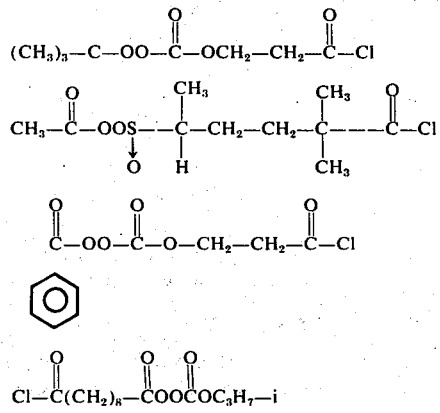

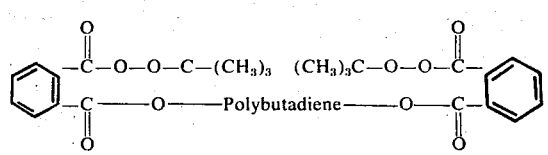

Polymers of the invention and the utility of certain compounds of the invention are illustrated by the following working examples:

EXAMPLE I

Reaction of hydroxyl terminated polybutadiene with t-butyl o(chloroformyl) peroxybenzoate

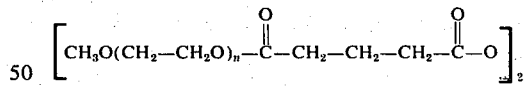

To a solution of 17.6g. of a hydroxyl-terminated polybutadiene liquid resin (equivalent weight 1330g. containing 0.75 meq/g) and triethylamine (1.4g.

0.0132 moles) in diethyl ether was added a solution of t-butyl o-(chloroformyl) peroxybenzoate (0.0132 moles) in benzene.

After filtration of the triethylamine hydrochloride and evaporation of the solvent a viscous liquid was obtained (16g.) that contained 0.27% A(O).

SPI exotherm in polyester resin at 115°C and 2% concentration gave the following:
Gel Time in minutes —15.1
Cure Time in minutes —22.0
Peak in °F — 332°

EXAMPLE II

Preparation of polyether containing an acylperoxy group $$\left[ CH_3O(CH_2-CH_2O)_n-\overset{O}{\underset{\|}{C}}-CH_2-CH_2-CH_2-\overset{O}{\underset{\|}{C}}-O \right]_2$$

To a solution of 15g. (0.02 moles) of a monohydroxyl-terminated polyether (Union Carbide Carbowax-750, molecular weight 715–785) and 2.02g. (0.02 moles) triethylamine in diethyl ether was added a solution of 3.2g (0.01 moles) bis[4-(chloroformyl)butyryl] peroxide in benzene.

The mixture was allowed to stir for six hours.

After filtration of the triethylamine hydrochloride, the ether solution was evaporated under reduced pressure.

A viscous liquid was obtained (16g.) containing 0.54% A(O).

n is 15–17 in the product formula.

EXAMPLE III

Reaction of hydroxyl-terminated polybutadiene with bis(4-chloroformylbutyryl) peroxide in presence of ethanol.

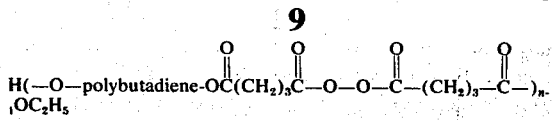

To a solution of 35.2g. of hydroxyl-terminated polybutadiene (Sinclair R-15 M resin) and 2g. (0.0264 moles) of triethylamine in diethyl ether was added a solution of bis(4-chloroformylbutyryl) peroxide (96.7%) (4.7g. 0.0132 moles) in diethyl ether.

After the addition was completed, absolute ethanol was added (1.2g. 0.0264 moles). The mixture was reacted for two hours. After filtration of the triethylamine hydrochloride, the ether solution was evaporated under reduced pressure. A viscous liquid was obtained (37g.) containing 0.30% A(O).

$n_1$ is greater than 1 in the product formula.

EXAMPLE IV

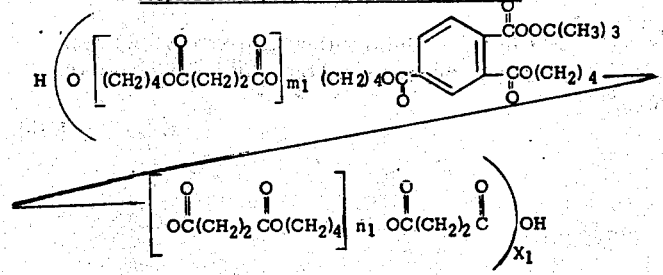

To 2.7g. (0.03 moles) of 1,4-butanediol and 7.5g. (0.075 moles) of triethylamine dissolved in diethyl ether was added a solution of 1.9g. (0.005 moles) t-butyl 2,4(5)-dichloroformyl) peroxybenzoate and 3.9g. (0.025 moles) of succinoyl dichloride in benzene.

After filtration of the triethylamine hydrochloride, the organic phase was stripped under vacuum. A viscous residue was obtained. SPI exotherm in polyester resin at 115°C and 1% concentration gave the following:

Gel Time in minutes —4.1
Cure Time in minutes —6.5
Peak in °F —385°

"$m_1$, $n_1$, and $X_1$" are each equal to more than 1 in the general formula shown for the polyester product.

EXAMPLE V

Preparation of block copolymer with styrene from product obtained in Example II

Polyether-Polystyrene

To 15g. of styrene placed in a tube is added 5g. of the product obtained on Example II. The tube is sealed under a nitrogen atmosphere and heated for seven hours at +10°C to +100°C. The polymer obtained from the reaction is dissolved in benzene and precipitated with odorless mineral spirit. The formation of the block copolymer is demonstrated by the demixing test similar to those of Hughes and Brown (4) and Molau (5): (4) L. J. Hughes and G. L. Brown, J. Appl. Polymer Sci.- 7-59 (1963); (5) G. E. Molau, J. Polymer Sci/43-1267 (1965). The control is a 50/50 mixture of 40% polystyrene and 40% solution of a monohydroxyl terminated polyether (Carbowax-750) in chloroform solution.

After these were well mixed the demixing time was 30 minutes. A 40% solution of the block prepared in chloroform showed no demixing in 22.5 hours.

A mixture of 1:1:1 of 40% solutions of polystyrene, Carbowax-750 and the prepared block in chloroform after they were well mixed showed a demixing time of 90 minutes.

EXAMPLE VI

Preparation of block copolymers with styrene from product obtained in Example III Polystyrene-Polybutadiene To 15g. of styrene placed in a tube is added 5g. of the product obtained in Example III. The tube is sealed under a nitrogen atmosphere and heated for seven hours at +70°C to +100°C. The polymer obtained from the reaction is dissolved in benzene and precipitated with odorless mineral spirit. The polymer is dried in a vacuum oven for 16 hours at +50°C and tested by the demixing test. (4)-(5).

The control is a 50/50 mixture of 15% polystyrene and 15% hydroxyl terminated polybutadiene in benzene solution. After these are well mixed, a demixing time of twenty minutes was obtained. A 15% solution of the block copolymer showed no demixing in 13 days. A mixture of 1:1:1 of 15% solutions of polystyrene, hydroxyl terminated polybutadiene and the block copolymer in benzene gave a demixing time of 6 hours.

EXAMPLE VII

Reaction of hydroxy-terminated polybutadiene-styrene with t-butyl o-(chloroformyl) peroxybenzoate

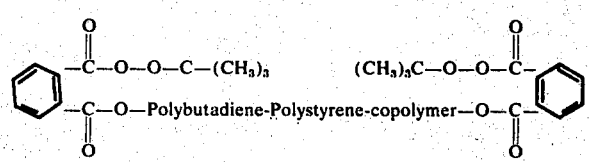

To a solution of 17.6g of hydroxyl-terminated polybutadiene polystyrene copolymer (Sinclair C-S-15 resin, equivalent weight 1330) containing 0.75 meq/gm) and triethylamine (1.4g. 0.0132 moles) in diethyl ether was added a solution of t-butyl o-(chloroformyl) peroxybenzoate (0.0132 moles) in benzene.

After filtration of the triethylamine hydrochloride and evaporation of the solvent a viscous liquid was obtained (16g.) that contained 0.43 A(O).

EXAMPLE VIII

Preparation of block copolymer with acrylonitrile from the copolymer containing peroxide in Example VII Polybutadiene-Polystyrene-Polyacrylonitrile Into a tube was placed 5g. of the copolymer containing peroxide (Example VII) and 60g. of toluene which is not a solvent for polyacrylonitrile.

The mixture was cooled at 0°C and 25g. of acrylonitrile was added. The tube was sealed under nitrogen and it was heated at 100°C for 27 hours.

A blank was prepared containing 0.5g. of polybutadienepolystyrene copolymer (Sinclair C-S-15), 2.5g. acrylonitrile and 6g. of toluene and it was heated at 100°C for 27 hours.

After this time the two solutions were cooled down to 23°-25°C and contrifugated for 4 hours. The blank failed to give any solid while the other sample separated 7g. of polyacrylonitrile.

The toluene solution after separation of the solid was precipitated with methanol and 12g. of solid was obtained. The increase weight of the soluble polymer was a proof of the block formation.

What is claimed is:

1. A peroxide having the formula

where:
1. R is hydrocarbon aliphatic of 1–20 carbons, cycloalkyl of 4–10 carbons or hydrocarbon aromatic of 6–12 carbons;
2. B is Cl— or Br—;
3. $R_1$ is tertiary alkyl of 4–8 carbons; and
4. $n$ and $m$ are integers equal to 1-2.

2. A peroxide as in claim 1 wherein B is Cl—.
3. A peroxide as in claim 2 wherein $R_1$ is t-butyl.
4. A peroxide as in claim 3 wherein R is phenyl.
5. A peroxide as in claim 3 wherein $n$ and $m$ are each 1.
6. t-Butyl o-(chloroformyl)peroxybenzoate.
7. 3-(t-Butylperoxycarbonyl)-propionyl chloride.

* * * * *